United States Patent
Xia et al.

(10) Patent No.: US 7,632,794 B1
(45) Date of Patent: Dec. 15, 2009

(54) LENS CARE SOLUTIONS COMPRISING ALKYLDIMONIUM HYDROXYPROPYL ALKYLGLUCOSIDES

(75) Inventors: Erning Xia, Penfield, NY (US);
Kimberly Millard, Rochester, NY (US);
Srini Venkatesh, Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 12/235,171

(22) Filed: Sep. 22, 2008

(51) Int. Cl.
*C11D 3/22* (2006.01)
*C11D 1/88* (2006.01)
*C11D 3/37* (2006.01)
*A61L 2/18* (2006.01)

(52) U.S. Cl. .................. 510/112; 510/470; 510/474; 510/490; 510/496; 510/504

(58) Field of Classification Search ........... 510/112, 510/470, 474, 490, 496, 504
See application file for complete search history.

(56) References Cited

U.S. PATENT DOCUMENTS

| | | | |
|---|---|---|---|
| 5,405,878 | A | 4/1995 | Ellis et al. |
| 6,277,365 | B1 | 8/2001 | Ellis |
| 7,192,937 | B2 | 3/2007 | Xia |
| 2009/0047232 | A1* | 2/2009 | Orubor et al. ............... 424/76.6 |

* cited by examiner

Primary Examiner—Brian P Mruk
(74) Attorney, Agent, or Firm—Joseph Barrera

(57) ABSTRACT

A contact lens care solution comprising one or more alkyldimonium hydroxypropyl alkylglucosides of general formula I or general formula II

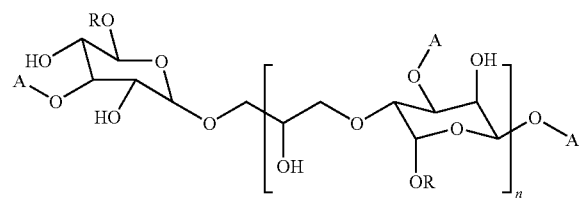

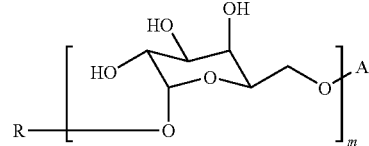

wherein R is a straight or branched $C_8$-$C_{24}$ alkyl;
A is $-CH_2CH(OH)CH_2N^+(CH_3)_2R^1X^-$, wherein $R^1$ is a $C_8$-$C_{24}$ alkyl and $X^-$ is a common counteranion, n is an average value from 1 to 6 and m is an average value from 1 to 2. The solution is formulated to clean and disinfect contact lenses or the solution is formulated as a rewet eye drop for use with contact lenses.

22 Claims, 3 Drawing Sheets

LENS CARE SOLUTIONS COMPRISING ALKYLDIMONIUM HYDROXYPROPYL ALKYLGLUCOSIDES

FIELD OF THE INVENTION

The present invention is directed to contact lens care solutions comprising one or more alkyldimonium hydroxypropyl alkylglucosides. The invention is also directed to a method of cleaning and disinfecting contact lenses by soaking the lenses in the solutions.

BACKGROUND OF THE INVENTION

During normal use, contact lenses become soiled or contaminated with a wide variety of compounds that can degrade lens performance. For example, a contact lens will become soiled with biological materials such as proteins or lipids that are present in the tear fluid and which adhere to the lens surface. Also, by handling of the contact lens, sebum (skin oil) or cosmetics or other materials can soil the contact lens. These biological and external contaminants can affect visual acuity and patient comfort. Accordingly, it is important to remove any debris from the lens surface for continued comfortable use with a lens care solution that contains one or more cleaning components.

Contact lens care solutions must also contain one or more antimicrobial components. Presently, the two most popular antimicrobial components are poly(hexamethylene biguanide), at times referred to as PHMB or PAPB, and polyquaternium-1. PHMB-based care solutions represent a significant improvement in patient comfort and antimicrobial effectiveness compared to most other antimicrobial components. However, as with any antimicrobial component there remains a tradeoff between the concentration of the antimicrobial component in the solution and the comfort experienced by the patient. Due to its wide commercial acceptance, extensive efforts have been directed to improve the antimicrobial efficacy or the comfort level to the patient by chemically modifying PHMB.

Those of ordinary skill in the art are also looking to other classes of antimicrobial compounds that could possibly improve upon the present PHMB-based or polyquaternium-1-based lens care solutions. Such compounds could possibly replace PHMB or polyquaternium-1 in the solutions. Alternatively, the compounds could be added to PHMB and polyquaternium-1 solutions to enhance the biocidal activity of the solutions.

Accordingly, this may allow one to formulate a lens care solution with relatively less amounts of PHMB or polyquaternium-1, and possibly improve upon other desired features such as greater comfort.

U.S. Pat. No. 7,192,937 describes ophthalmic compositions containing one or more oligosaccharides in an amount effective to disinfect or preserve contact lenses, as a rewet drop for contact lenses or to preserve pharmaceutical formulations. A particular oligosaccharide described in U.S. Pat. No. 7,192,937 is stearyl dihydroxypropyldimonoim oligiosaccharide (SDO) of general formula

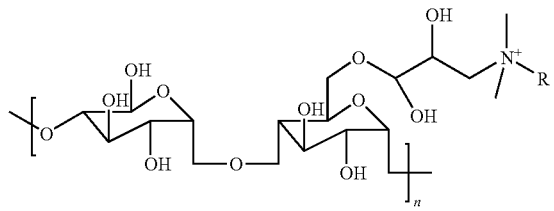

SDO is sold under the tradename Oligioquat® M and is available from Arch Chemicals, S. Plainfield, N.J., and has a reported weight average molecular weight of 25 k to 50 k. The compositions also include an aminoalcohol buffer and a tonicity agent.

U.S. Pat. No. 6,277,365 describes ophthalmic compositions containing one or more ethoxylated glycosides with a quaternary nitrogen (alkyldimonoim). The compositions can be used to disinfect or preserve contact lenses, as a rewet drop for contact lenses or to preserve pharmaceutical formulations. A particular ethoxylated glycoside described in U.S. Pat. No. 6,277,365 is of general formula

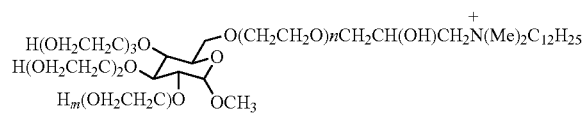

Glucoquat® 100 is available from Amerchol Corp, Edison, N.J. The compositions can also include a disinfectant such as poly(hexamethylene biguanide) and a therapeutic agent including dry eye agent such as hyaluronic acid or a drug for ophthalmic applications.

SUMMARY OF THE INVENTION

The alkyldimonium hydroxypropyl alkylglucosides are used as a component in a contact lens care solution such as a lens care multipurpose solution or in a contact lens rewet eyedrop. Accordingly, the invention is directed to a contact lens care solution comprising one or more alkyldimonium hydroxypropyl alkylglucosides of general formula I or general formula II

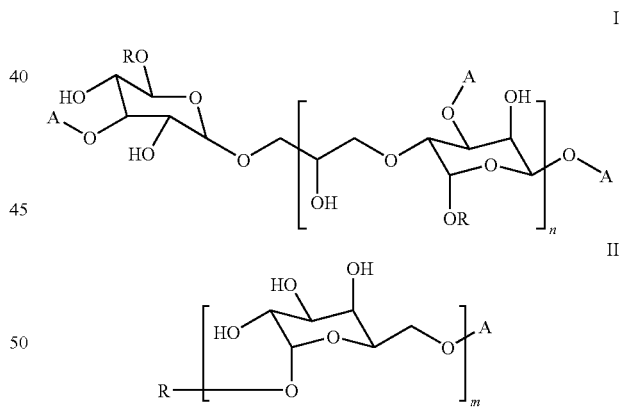

wherein R is a straight or branched $C_8$-$C_{24}$alkyl;

A is $-CH_2CH(OH)CH_2N^+(CH_3)_2R^1X^-$, wherein $R^1$ is a $C_8$-$C_{24}$alkyl and $X^-$ is a common counteranion, n is an average value from 1 to 6 and m is an average value from 1 to 2. The solution is formulated to clean and disinfect contact lenses or the solution is formulated as a rewet eye drop for use with contact lenses.

BRIEF DESCRIPTION OF THE DRAWINGS

The invention will be better understood from the following description and in consideration with the accompanying Figures. It is to be expressly understood, however, that each of the FIG. 1 is a bar graph showing the intensity of fluorescence units of a sodium fluorescein permeability assay with HCEC for two commercial lens care solutions, and compositions of the invention in buffered borate solution.

DETAILED DESCRIPTION OF THE INVENTION

Figure 1:
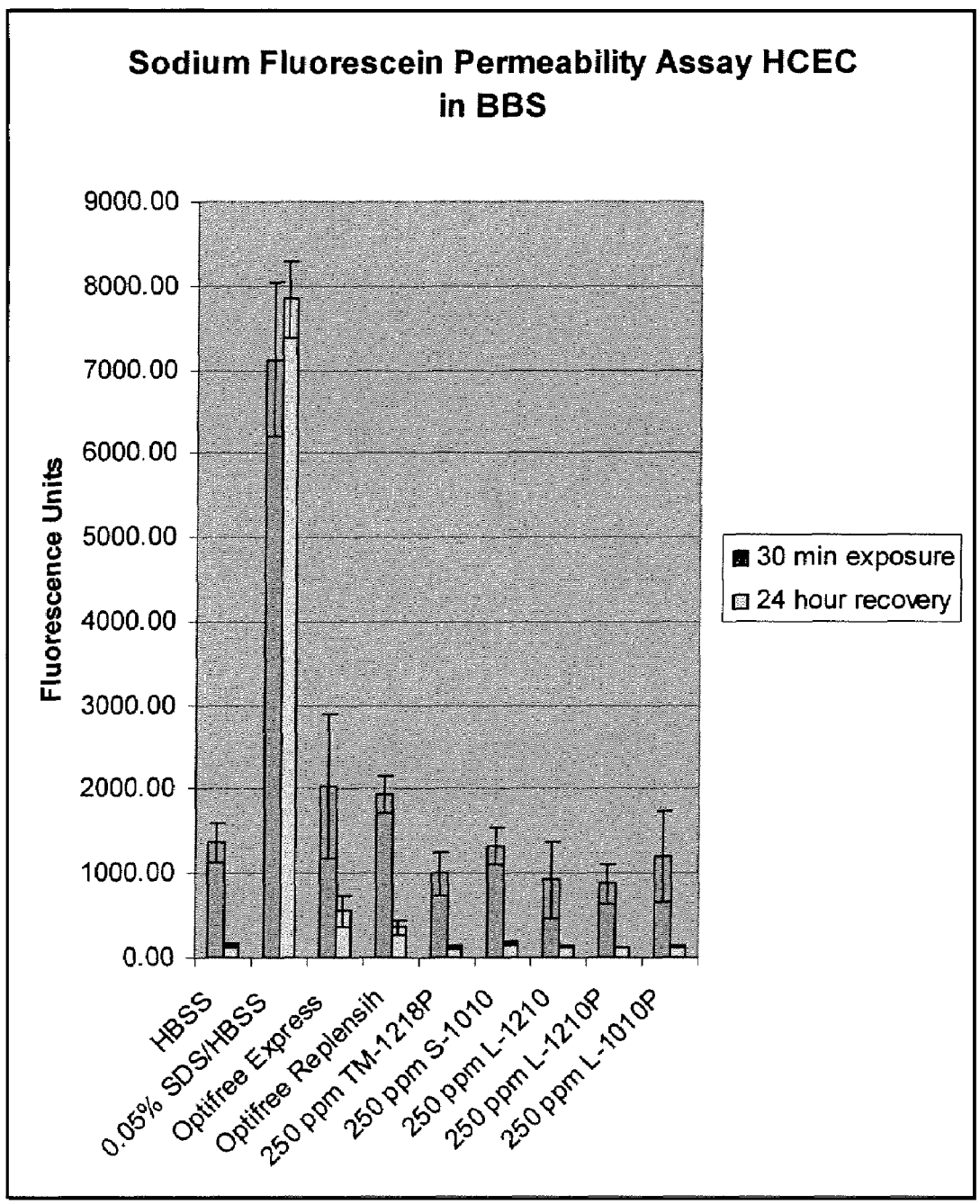

The invention is directed to a contact lens care solution comprising one or more alkyldimonium hydroxypropyl alkylglucosides of general formula I or general formula II

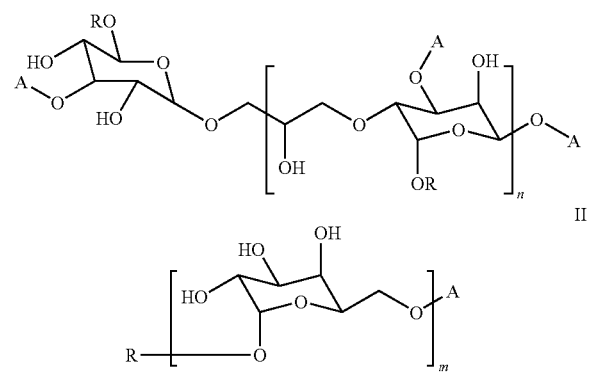

wherein R is a straight or branched $C_8$-$C_{24}$alkyl;

A is —$CH_2CH(OH)CH_2N^+(CH_3)_2R^1X^-$, wherein $R^1$ is a $C_8$-$C_{24}$alkyl and $X^-$ is a common counteranion, n is an average value from 1 to 6 and m is an average value from 1 to 2. The solution is formulated to clean and disinfect contact lenses or the solution is formulated as a rewet eyedrop for use with contact lenses.

Some of the more preferred alkyldimonium hydroxypropyl alkylglucosides of general formula I is selected from the group consisting of stearyldimonium hydroxypropyl laurylglucosides chloride, stearyldimonium hydroxypropyl laurylglucosides chloride, stearyldimonium hydroxypropyl decylglucosides chloride, lauryldimonium hydroxypropyl laurylglucosides chloride, lauryldimonium hydroxypropyl decylglucosides chloride and trimonium hydroxypropyl cocoglucosides chloride.

Some of the more preferred alkyldimonium hydroxypropyl alkylglucoside of general formula II is selected from the group consisting of Polystearyldimoniumhydroxypropyl laurylglucosides chloride, Polystearyldimoniumhydroxypropyl decylglucosides chloride, Polylauryldimoniumhydroxypropyl laurylglucosides chloride, Polylauryldimoniumhydroxypropyl decylglucosides chloride, Polytrimoniumhydroxypropyl laurylglucosides chloride and Polytrimoniumhydroxypropyl decylglucosides chloride.

Following the testing of a number of commercially available alkyldimonium hydroxypropyl alkylglucosides of general formula I and general formula II, Applicants observed that that both stearyl dimoniumhydropropyl laurylglucoside and stearyl dimoniumhydropropyl decylglucoside exhibit a relatively high increase in biocidal efficacy in an aqueous buffered borate solution. In particular, against the three bacterium and two fungal strains tested a combination of stearyl dimoniumhydropropyl laurylglucoside and stearyl dimoniumhydropropyl decylglucoside appeared to provide the optimal biocidal efficacy.

In many formulations, the one or more alkyldimonium hydroxypropyl alkylglucosides of general formula I or general formula II are each present in the formulation from 0.001% to 0.1% by weight. In other embodiments, the one or more alkyldimonium hydroxypropyl alkylglucosides of general formula I or general formula II are each present in the formulation from 0.001% to 0.05% by weight. In still another embodiment, the one or more alkyldimonium hydroxypropyl alkylglucosides of general formula I or general formula II are each present in the formulation from 0.003% to 0.015% by weight.

As stated, the compositions can also include a cationic antimicrobial component selected from quaternary ammonium compounds (including small molecules) and polymers and low and high molecular weight biguanides. For example, biguanides include the free bases or salts of alexidine, chlorhexidine, hexamethylene biguanides and their polymers, and combinations thereof. The salts of alexidine and chlorhexidine can be either organic or inorganic and include gluconates, nitrates, acetates, phosphates, sulfates, halides and the like.

In a preferred embodiment, the composition will include a polymeric biguanide known as poly(hexamethylene biguanide) (PHMB or PAPB) commercially available from Zeneca, Wilmington, Del. as Cosmocil® CQ. The PHMB is present in the compositions from 0.2 ppm to 5 ppm or from 0.5 ppm to 2 ppm.

Other cationic antimicrobial components include quaternary ammonium compounds including those compounds generically referred to in the art as polyquaternium. They are identified by a particular number following the designation such as polyquaternium-1, polyquaternium-10 or polyquaternium-42. In general, polyquaternium polymers are a well-known class of commercially available polymers. The polyquaternium polymer preferably includes an opthalmologically suitable anionic organic or inorganic counterion. A preferred counterion may include, but are not limited to fluoride ions, chloride ions, bromide ions, iodide ions and the like.

Accordingly, the contact lens care solutions can include one or more antimicrobial components in addition to the one or more alkyldimonium hydroxypropyl alkylglucosides of general formula I or general formula II. Applicants have determined that one can actually enhance the biocidal efficacy of a contact lens solution comprising PHMB or polyquaternium-1 by adding an alkyldimonium hydroxypropyl alkylglucosides of general formula I or general formula II to the solution. The addition of the alkyldimonium hydroxypropyl alkylglucosides to the solution allows one of ordinary skill to formulate a lens care solution with lower concentrations of PHMB or polyquaternium-1, yet maintain a high acceptable level of antimicrobial activity It is to be understood by those in the art that the contact lens care solutions can include one or more of the cationic antimicrobial components described above. For example, in one embodiment, the lens care solutions include polyquaternium-1 in combination with a biguanide antimicrobial component such as poly(hexamethylene biguanide). The polyquaternium-1 is present in relatively low concentrations, that is, from 0.5 ppm to 5 ppm, relative to the reported concentration of polyquaternium-1 in both Opti-Free® and Opti-Free® Replenish. The PHMB is present at concentrations from 0.3 ppm to 1.5 ppm, Applicants believe that the polyquaternium-1 and PHMB, in combination, may enhance the biocidal efficacy of the lens care solutions. The addition of the alkyldimonium hydroxypropyl alkylglucosides of general formula I or general formula II can provide an additional antimicrobial benefit to the solutions.

The contact lens care solution will also contain one or more surfactants. One particular class of surfactants used in contact lens care solutions includes amphoteric surfactants. An exemplary amphoteric surfactant is of general formula A

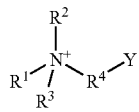

A wherein $R^1$ is R or $—(CH_2)_n—NHC(O)R$, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$.

In many embodiments, the amphoteric surfactant of general formula A is a sulfobetaine of general formula B

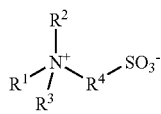

B wherein $R^1$ is a $C_8$-$C_{30}$alkyl; $R^2$ and $R^3$ are each independently selected from a $C_1$-$C_4$alkyl; and $R^4$ is a $C_2$-$C_8$alkylene.

Certain sulfobetaines of general formula B are more preferred than others. For example, Zwitergent®3-10 available from Calbiochem Company, is a sulfobetaine of general formula I wherein $R^1$ is a straight, saturated alkyl with ten (10) carbons, $R^2$ and $R^3$ are each methyl and $R^4$ is $—CH_2CH_2CH_2—$ (three carbons, (3)). Other sulfobetaines that can be used in the ophthalmic compositions include the corresponding Zwitergent®3-08 ($R^1$ is a is a straight, saturated alkyl with eight carbons), Zwitergent® 3-12 ($R^1$ is a is a straight, saturated alkyl with twelve carbons), Zwitergent®3-14 ($R^1$ is a is a straight, saturated alkyl with fourteen carbons) and Zwitergent® 3-16 ($R^1$ is a is a straight, saturated alkyl with sixteen carbons). Accordingly, some of the more preferred the contact lens carte solutions will include a sulfobetaine of general formula B wherein $R^1$ is a $C_8$-$C_{16}$alkyl and $R^2$ and $R^3$ is methyl.

In another embodiment, the amphoteric surfactant of general formula A is a hydroxysulfobetaine of general formula C

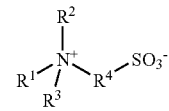

C wherein $R^1$ is a $C_8$-$C_{30}$alkyl substituted with at least one hydroxyl; $R^2$ and $R^3$ are each independently selected from a $C_1$-$C_4$alkyl; and $R^4$ is a $C_2$-$C_8$alkylene substituted with at least one hydroxyl.

In another embodiment, the amphoteric surfactant is an alkylamido betaine of general formula D

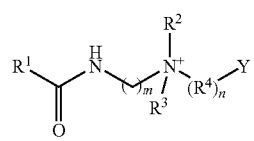

D wherein $R^1$ is a $C_8$-$C_{30}$alkyl, and m and n are independently selected from 2, 3, 4 or 5; $R^2$ and $R^3$ are each independently selected from a $C_1$-$C_4$alkyl optionally substituted with hydroxyl; $R^4$ is a $C_2$-$C_8$alkylene optionally substituted with hydroxyl; and Y is $CO_2—$ or $SO_3—$. The most common alkylamido betaines are alkylamidopropyl betaines, e.g., cocoamidopropyl dimethyl betaine and lauroyl amidopropyl dimethyl betaine.

The above amphoteric surfactants will generally be present in a total amount from 0.01% to 1% w/v, from 0.01% to 0.5% w/v, or from 0.1% to 0.2% w/v.

Another class of surfactants used in contact lens cares solutions include the poly(oxypropylene)-poly(oxyethylene) block copolymer type of nonionic surfactants. One type of copolymer surfactant is an adduct of ethylene diamine having a molecular weight from about 6,000 to about 24,000 daltons wherein at least 40 weight percent of said adduct is poly (oxyethylene) has been found to be particularly advantageous for use in cleaning and conditioning both soft and hard contact lenses. The CTFA Cosmetic Ingredient Dictionary's adopted name for this group of surfactants is poloxamine. Such surfactants are available from BASF Wyandotte Corp., Wyandotte, Mich., under Tetronic®. Particularly good results are obtained with poloxamine 1107 or poloxamine 1304. The poly(oxyethylene) poly(oxypropylene) block polymer surfactants will generally be present in a total amount from 0.1% to 2% w/v, from 0.1% to 1% w/v, or from 0.2% to 0.8% w/v.

An analogous of series of surfactants, for use in the lens care compositions, is the poloxamer series which is a poly (oxyethylene) poly(oxypropylene) block polymers available under Pluronic® (commercially available form BASF). In accordance with one embodiment of a lens care composition the poly(oxyethylene)-poly(oxypropylene) block copolymers will have molecular weights from 2500 to 13,000 daltons or from 6000 to about 12,000 daltons. Specific examples of surfactants which are satisfactory include: poloxamer 108, poloxamer 188, poloxamer 237, poloxamer 238, poloxamer 288 and poloxamer 407. Particularly good results are obtained with poloxamer 237 or poloxamer 407. The foregoing poly(oxyethylene) poly(oxypropylene) block polymer surfactants will generally be present in a total amount from 0.0 to 2% w/v, from 0. to 1% w/v, or from 0.2 to 0.8% w/v.

The contact lens care solutions will very likely include a buffer system. By the terms "buffer" or "buffer system" is meant a compound that, usually in combination with at least one other compound, provides a buffering system in solution that exhibits buffering capacity, that is, the capacity to neutralize, within limits, either acids or bases (alkali) with relatively little or no change in the original pH. Generally, the buffering components are present from 0.05% to 2.5% (w/v) or from 0.1% to 1.5% (w/v).

The term "buffering capacity" is defined to mean the millimoles (mM) of strong acid or base (or respectively, hydrogen or hydroxide ions) required to change the pH by one unit when added to one liter (a standard unit) of the buffer solution. The buffer capacity will depend on the type and concentration of the buffer components. The buffer capacity is measured from a starting pH of 6 to 8, preferably from 7.4 to 8.4.

Borate buffers include, for example, boric acid and its salts, for example, sodium borate or potassium borate. Borate buffers also include compounds such as potassium tetraborate or potassium metaborate that produce borate acid or its salt in solutions. Borate buffers are known for enhancing the efficacy of certain polymeric biguanides. For example, U.S. Pat. No. 4,758,595 to Ogunbiyi et al. describes that a contact-lens solution containing PHMB can exhibit enhanced efficacy if combined with a borate buffer.

A phosphate buffer system preferably includes one or more monobasic phosphates, dibasic phosphates and the like. Particularly useful phosphate buffers are those selected from phosphate salts of alkali and/or alkaline earth metals. Examples of suitable phosphate buffers include one or more of sodium dibasic phosphate ($Na_2HPO_4$), sodium monobasic phosphate ($NaH_2PO_4$) and potassium monobasic phosphate ($KH_2PO_4$). The phosphate buffer components frequently are used in amounts from 0.01% or to 0.5% (w/v), calculated as phosphate ion.

Other known buffer compounds can optionally be added to the lens care compositions, for example, citrates, citric acid, sodium bicarbonate, TRIS, and the like. Other ingredients in the solution, while having other functions, may also affect the buffer capacity, e.g., propylene glycol or glycerin.

A preferred buffer system is based upon boric acid/borate, a mono and/or dibasic phosphate salt/phosphoric acid or a combined boric/phosphate buffer system. For example a combined boric/phosphate buffer system can be formulated from a mixture of boric acid/sodium borate and a monobasic/dibasic phosphate. In a combined boric/phosphate buffer system, the phosphate buffer is used (in total) at a concentration of 0.004 to 0.2 M (Molar), preferably 0.04 to 0.1 M. The borate buffer (in total) is used at a concentration of 0.02 to 0.8 M, preferably 0.07 to 0.2 M.

The lens care solutions can also include a phosphonic acid, or its physiologically compatible salt, that is represented by the following formula:

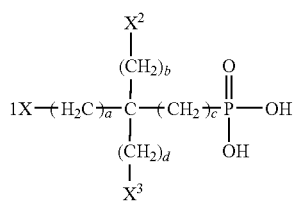

wherein each of a, b, c, and d are independently selected from integers from 0 to 4, preferably 0 or 1; $X^1$ is a phosphonic acid group (i.e., $P(OH)_2O$), hydroxy, amine or hydrogen; and $X^2$ and $X^3$ are independently selected from the group consisting of halogen, hydroxy, amine, carboxy, alkylcarbonyl, alkoxycarbonyl, or substituted or unsubstituted phenyl, and methyl. Exemplary substituents on the phenyl are halogen, hydroxy, amine, carboxy and/or alkyl groups. A particularly preferred species is that wherein a, b, c, and d in are zero, specifically the tetrasodium salt of 1-hydroxyethylidene-1,1-diphosphonic acid, also referred to as tetrasodium etidronate, commercially available from Monsanto Company as DeQuest® 2016 diphosphonic acid sodium salt or phosphonate.

The lens care solutions can include dexpanthenol, which is an alcohol of pantothenic acid, also called Provitamin B5, D-pantothenyl alcohol or D-panthenol. It has been stated that dexpanthenol may play a role in stabilizing the lachrymal film at the eye surface following placement of a contact lens on the eye. Dexpanthenol is preferably present in the solution in an amount from 0.2 to 5%/v, from 0.5 to 3% w/v, or from 1 to 2% w/v.

The contact lens care solutions can also include a sugar alcohol such as sorbitol or xylitol. Typically, dexpanthenol is used in combination with the sugar alcohol. The sugar alcohol is present in the lens care compositions in an amount from 0.4 to 5% w/v or from 0.8 to 3% w/v.

The lens care solutions can also include one or more neutral or basic amino acids. The neutral amino acids include: the alkyl-group-containing amino acids such as alanine, isoleucine, valine, leucine and proline; hydroxyl-group-containing amino acids such as serine, threonine and 4-hydroxyproline; thio-group-containing amino acids such as cysteine, methionine and asparagine. Examples of the basic amino acid include lysine, histidine and arginine. The one or more neutral or basic amino acids are present in the compositions at a total concentration of from 0.1 to 3% w/v.

The lens care solutions can also include glycolic acid, asparatic acid or any mixture of the two at a total concentration of from 0.001% to 4% (w/v) or from 0.01% to 2.0% (w/v). In addition, the combined use of one or more amino acids and glycolic acid and/or asparatic acid can lead to a reduction in the change of the size of the contact lens due to swelling and shrinkage following placement in the lens solution.

The lens care solutions can also include one or more comfort or cushioning components. The comfort component can enhance and/or prolong the cleaning and wetting activity of the surfactant component and/or condition the lens surface rendering it more hydrophilic (less lipophilic) and/or to act as a demulcent on the eye. The comfort component is believed to cushion the impact on the eye surface during placement of the lens and serves also to alleviate eye irritation.

Suitable comfort components include, but are not limited to, water soluble natural gums, cellulose-derived polymers and the like. Useful natural gums include guar gum, gum tragacanth and the like. Useful cellulose-derived comfort components include cellulose-derived polymers, such as hydroxypropyl cellulose, hydroxypropylmethyl cellulose, carboxymethyl cellulose, methyl cellulose, hydroxyethyl cellulose and the like. A very useful comfort component is hydroxypropylmethyl cellulose (HPMC). Some non-cellulose comfort components include hydroxypropyl guar, propylene glycol or glycerin. The comfort components are typically present in the solution from 0.01% to 1% (w/v).

One particular comfort agent that exhibits a preference among contact lens patients is hyaluronic acid. Hyaluronic acid is a linear polysaccharide (long-chain biological polymer) formed by repeating disaccharide units consisting of D-glucuronic acid and N— acetyl-D-glucosamine linked by β(1-3) and β(1-4) glycosidic linkages. Hyaluronic acid is distinguished from the other glycosaminoglycans, as it is free from covalent links to protein and sulphonic groups. Hyaluronic acid is ubiquitous in animals, with the highest concentration found in soft connective tissue. It plays an important role for both mechanical and transport purposes in the body; e.g., it gives elasticity to the joints and rigidity to the vertebrate disks, and it is also an important component of the vitreous body of the eye.

Hyaluronic acid is accepted by the ophthalmic community as a compound that can protect biological tissues or cells from compressive forces. Accordingly, hyaluronic acid has been proposed as one component of a viscoelastic ophthalmic composition for cataract surgery. The viscoelastic properties of hyaluronic acid, that is, hard elastic under static conditions though less viscous under small shear forces enables hyaluronic acid to basically function as a shock absorber for cells and tissues. Hyaluronic acid also has a relatively large capacity to absorb and hold water. The stated properties of hyaluronic acid are dependent on the molecular weight, the solution concentration, and physiological pH. At low concentrations, the individual chains entangle and form a continuous network in solution, which gives the system interesting properties, such as pronounced viscoelasticity and pseudoplasticity that is unique for a water-soluble polymer at low concentration.

Another preferred comfort agent that is believed to maintain a hydrated corneal surface is polyvinylpyrrolidone (PVP). PVP is a linear homopolymer or essentially a linear homopolymer comprising at least 90% repeat units derived from 1-vinyl-2-pyrrolidone monomer, the remainder of the monomer composition can include neutral monomer, e.g., vinyl or acrylates. Other synonyms for PVP include povidone, polyvidone, 1-vinyl-2-pyrrolidinone, and 1-ethenyl-2-pyrolionone (CAS registry number 9003-39-8). The PVP will preferably have a weight average molecular weight from 10,000 to 250,000 or from 30,000 to 100,000. Such materials are sold by various companies, including ISP Technologies, Inc. under the trademark PLASDONE® K-29/32, from BASF under the trademark KOLLIDON®, for example, KOLLIDON® K-30 or K-90. It is also preferred that one use pharmaceutical grade PVP.

The lens care solutions can also include one or more chelating components to assist in the removal of lipid and protein deposits from the lens surface following daily use. Typically, the ophthalmic compositions will include relatively low amounts, e.g., from 0.005% to 0.05% (w/v) of ethylenediaminetetraacetic acid (EDTA) or the corresponding metal salts thereof such as the disodium salt, $Na_2EDTA$.

One possible alternative to the chelator $Na_2EDTA$ or a possible combination with $Na_2EDTA$, is a disuccinate of formula IV below or a corresponding salt thereof;

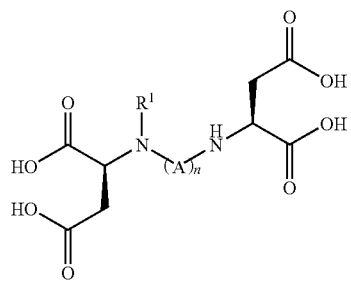

IV wherein $R_1$ is selected from hydrogen, alkyl or —C(O)alkyl, the alkyl having one to twelve carbons and optionally one or more oxygen atoms, A is a methylene group or an oxyalkylene group, and n is from 2 to 8. In one embodiment, the disuccinate is S,S— ethylenediamine disuccinate (S,S-EDDS) or a corresponding salt thereof. One commercial source of S,S-EDDS is represented by Octaquest® E30, which is commercially available from Octel. The chemical structure of the trisodium salt of S,S-EDDS is shown below. The salts can also include the alkaline earth metals such as calcium or magnesium. The zinc or silver salt of the disuccinate can also be used in the ophthalmic compositions.

Still another class of chelators include alkyl ethylenediaminetriacetates such as nonayl ethylenediaminetriacetate. See, U.S. Pat. No. 6,995,123 for a more complete description of such agents.

The lens care solutions will typically include an effective amount of a tonicity adjusting component. Among the suitable tonicity adjusting components that can be used are those conventionally used in contact lens care products such as various inorganic salts. Sodium chloride and/or potassium chloride and the like are very useful tonicity components. The amount of tonicity adjusting component is effective to provide the desired degree of tonicity to the solution.

The lens care solutions will typically have an osmolality in the range of at least about 200 mOsmol/kg for example, about 300 or about 350 to about 400 mOsmol/kg. The lens care solutions are substantially isotonic or hypertonic (for example, slightly hypertonic) and are ophthalmically acceptable.

One exemplary ophthalmic composition is formulated as a contact lens disinfecting solution prepared with the components and amounts of each listed in Table 1.

Another contact lens solution according to the present invention includes the following ingredients listed in Table 2.

Another contact lens solution according to the present invention includes the following ingredients listed in Table 3.

Another contact lens solution according to the present invention includes the following ingredients listed in Table 4.

TABLE 1

| Component | Minimum Amount (wt. %) | Maximum Amount (wt. %) | Preferred Amount (wt. %) |
| --- | --- | --- | --- |
| boric acid | 0.1 | 1.0 | 0.6 |
| sodium borate | 0.01 | 0.2 | 0.1 |
| sodium chloride | 0.2 | 0.8 | 0.5 |
| zwitergent ® 3-10 | 0.005 | 0.3 | 0.05 |
| S-1218 | 0.001 | 0.1 | 0.01 |
| Tetronic ® 1107 | 0.05 | 2.0 | 1.0 |
| hyaluronic acid | 0.005 | 0.04 | 0.01 |
| $Na_2EDTA$ | 0.005 | 0.15 | 0.03 |
| PHMB | 0.2 ppm | 2 ppm | 1.3 ppm |
| polyquaternium-1 | 0.5 ppm | 5 ppm | 1 ppm |

TABLE 2

| Component | Minimum Amount (wt. %) | Maximum Amount (wt. %) | Preferred Amount (wt. %) |
| --- | --- | --- | --- |
| sorbitol or xylitol | 0.5 | 5 | 3 |
| poloxamer 407 | 0.05 | 1.0 | 0.4 |
| sodium phosphate, dihydrogen | 0.10 | 0.8 | 0.5 |
| dexpanthenol | 0.01 | 1.0 | 0.03 |
| zwitergent ® 3-10 | 0.01 | 0.2 | 0.05 |
| S-1218 | 0.005 | 0.1 | 0.01 |

TABLE 2-continued

| Component | Minimum Amount (wt. %) | Maximum Amount (wt. %) | Preferred Amount (wt. %) |
|---|---|---|---|
| Na$_2$EDTA | 0.005 | 0.3 | 0.1 |
| PHMB | 0.2 ppm | 2 ppm | 1 ppm |

TABLE 3

| Component | Minimum Amount (wt. %) | Maximum Amount (wt. %) | Preferred Amount (wt. %) |
|---|---|---|---|
| NaCl/KCl | 0.2 | 1.0 | 0.5 |
| propylene glycol | 0.1 | 1.0 | 0.5 |
| poloxamer 237 | 0.01 | 1.0 | 0.5 |
| phosphate monobasic | 0.05 | 0.4 | 0.1 |
| phosphate dibasic | 0.05 | 0.4 | 0.12 |
| zwitergent ® 3-10 | 0.01 | 0.3 | 0.1 |
| S-1218 | 0.005 | 0.1 | 0.01 |
| Na$_2$EDTA | 0.005 | 0.3 | 0.1 |
| PHMB | 0.2 ppm | 2 ppm | 1.1 ppm |
| polyquaternium-1 | 0.5 ppm | 5 ppm | 1 ppm |

TABLE 4

| Component | Minimum Amount (wt. %) | Maximum Amount (wt. %) | Preferred Amount (wt. %) |
|---|---|---|---|
| NaCl/KCl | 0.01 | 0.5 | 0.1 |
| sorbitol | 0.2 | 2.0 | 0.5 |
| Propylene glycol | 0.2 | 2.0 | 0.6 |
| Poloxamine 1304 | 0.05 | 1.0 | 0.5 |
| Boric acid | 0.1 | 1.0 | 0.6 |
| Sodium borate | 0.01 | 0.2 | 0.1 |
| Hydroxypropyl guar | 0.01 | 0.5 | 0.05 |
| zwitergent ® 3-10 | 0.01 | 0.4 | 0.05 |
| S-1218 | 0.005 | 0.1 | 0.01 |
| Na$_2$EDTA | 0.02 | 0.1 | 0.05 |
| PHMB | 0.2 ppm | 2 ppm | 0.3 ppm |
| polyquaternium-1 | 0.5 ppm | 5 ppm | 1.3 ppm |

Another contact lens solution according to the present invention includes the following ingredients listed in Table 5.

TABLE 5

| Component | Minimum Amount (wt. %) | Maximum Amount (wt. %) | Preferred Amount (wt. %) |
|---|---|---|---|
| NaCl/KCl | 0.05 | 0.5 | 0.1 |
| phosphate monobasic | 0.05 | 0.4 | 0.12 |
| phosphate dibasic | 0.05 | 0.4 | 0.21 |
| sorbitol | 0.5 | 2.0 | 1.0 |
| Poloxamine 904 | 0.02 | 1.0 | 0.5 |
| Povidone K90 | 0.05 | 0.5 | 0.1 |
| zwitergent ® 3-10 | 0.01 | 0.2 | 0.05 |
| S-1218 | 0.005 | 0.1 | 0.01 |
| Na$_2$EDTA | 0.005 | 0.3 | 0.1 |
| PHMB | 0.2 ppm | 2 ppm | 1 ppm |

As described, the ophthalmic compositions can be used to clean and disinfect contact lenses. In general, the contact lens solutions can be used as a daily or every other day care regimen known in the art as a "no-rub" regimen. This procedure includes removing the contact lens from the eye, rinsing both sides of the lens with a few milliliters of solution and placing the lens in a lens storage case. The lens is then immersed in fresh solution for at least two hours. The lens is the removed form the case, optionally rinsed with more solution, and repositioned on the eye.

Alternatively, a rub protocol would include each of the above steps plus the step of adding a few drops of the solution to each side of the lens, followed by gently rubbing the surface between ones fingers for approximately 3 to 10 seconds. The lens can then be, optionally rinsed, and subsequently immersed in the solution for at least two hours. The lenses are removed from the lens storage case and repositioned on the eye.

The ophthalmic compositions can be used with many different types of contact lenses including: (1) hard lenses formed from materials prepared by polymerization of acrylic esters, such as poly(methyl methacrylate) (PMMA), (2) rigid gas permeable (RGP) lenses formed from silicone acrylates and fluorosilicone methacrylates, (3) soft, hydrogel lenses, and (4) non-hydrogel elastomer lenses.

As an example, soft hydrogel contact lenses are made of a hydrogel polymeric material, a hydrogel being defined as a crosslinked polymeric system containing water in an equilibrium state. In general, hydrogels exhibit excellent biocompatibility properties, i.e., the property of being biologically or biochemically compatible by not producing a toxic, injurious or immunological response in a living tissue. Representative conventional hydrogel contact lens materials are made by polymerizing a monomer mixture comprising at least one hydrophilic monomer, such as (meth)acrylic acid, 2-hydroxyethyl methacrylate (HEMA), glyceryl methacrylate, N,N-dimethacrylamide, and N-vinylpyrrolidone (NVP). In the case of silicone hydrogels, the monomer mixture from which the copolymer is prepared further includes a silicone-containing monomer, in addition to the hydrophilic monomer. Generally, the monomer mixture will also include a crosslink monomer such as ethylene glycol dimethacrylate, tetraethylene glycol dimethacrylate, and methacryloxyethyl vinylcarbonate. Alternatively, either the silicone-containing monomer or the hydrophilic monomer may function as a crosslink agent.

EXAMPLES 1-9

Data obtained from a four hour dose response study of S1218 in borate-buffered solution (BBS) is provided in Table A. The concentration of S1218 for each example composition is stated in (ppm).

TABLE A

Four hour dose response of S1218 in BBS.

| | microbe | | | | |
|---|---|---|---|---|---|
| Ex. No. | S. aureus | P. aeruginosa | S. marcescens | C. albicans | F. solani |
| BBS control | 1.3 | 1.1 | 1.1 | 0.5 | 0.6 |
| 1, (1000) | >4.7 | >4.6 | 4.6 | >4.6 | >4.1 |
| 2, (500) | >4.7 | >4.6 | >4.6 | >4.7 | >4.1 |
| 3, (250) | >4.7 | >4.6 | 4.6 | 4.5 | >4.1 |
| 4, (125) | >4.7 | 4.1 | 4.1 | 3.7 | >4.1 |
| 5, (62.5) | 4.5 | 4.0 | 2.3 | 2.0 | 3.7 |
| 6, (31.3) | 2.7 | 2.4 | 1.1 | 1.4 | 1.9 |
| 7, (15.6) | 1.7 | 1.1 | 1.1 | 0.5 | 1.1 |
| 8, (7.8) | 1.4 | 1.1 | 1.1 | 0.6 | 0.7 |
| 9, (3.9) | 1.2 | 1.1 | 1.1 | 0.6 | 0.5 |

EXAMPLES 10-18

Data obtained from a four hour dose response study of S1010P in borate-buffered solution (BBS) is provided in Table B. The concentration of S1010P for each example composition is stated in (ppm).

TABLE B

Four hour dose response of S1010P in BBS.

| Ex. No. | microbe | | | | |
|---|---|---|---|---|---|
| | S. aureus | P. aeruginosa | S. marcescens | C. albicans | F. solani |
| BBS control | 1.3 | 1.1 | 1.1 | 0.5 | 0.6 |
| 10, (1000) | >4.8 | >4.6 | >4.6 | >4.8 | >4.4 |
| 11, (500) | >4.8 | >4.6 | >4.6 | >4.8 | >4.4 |
| 12, (250) | >4.8 | >4.6 | >4.6 | >4.8 | >4.4 |
| 13, (125) | >4.8 | 3.9 | 3.3 | 2.8 | 3.7 |
| 14, (62.5) | >4.8 | 3.4 | 1.8 | 1.1 | 1.9 |
| 15, (31.3) | 3.2 | 2.2 | 1.1 | 0.5 | 0.8 |
| 16, (15.6) | 2.0 | 1.1 | 1.1 | 0.5 | 0.5 |
| 17, (7.8) | 2.0 | 1.1 | 1.1 | 0.4 | 0.4 |
| 18, (3.9) | 1.3 | 1.1 | 1.1 | 0.5 | 0.3 |

EXAMPLES 19 AND 20

Data obtained from a four hour dose response study of S1218 in borate-buffered solution (BBS) with an osmolality of 330 Osm/kg is provided in Table C. Comparative Examples A and B contain 1.3 ppm PHMB and 0.8 ppm PHMB, respectively, in corresponding BBS. Example 19 contains 100 ppm S1218 in BBS. Example 20 contains 100 ppm S1218 and 0.8 ppm PHMB in BBS.

TABLE C

Four hour dose response of S1218 with PHMB in BBS.

| Ex. No. | microbe | | | | |
|---|---|---|---|---|---|
| | S. aureus | P. aeruginosa | S. marcescens | C. albicans | F. solani |
| BBS control | 1.5 | 1.2 | 1.3 | 0.6 | 0.4 |
| Comp. Ex. A | 2.6 | 3.6 | 2.7 | 2.3 | 2.2 |
| Comp. Ex. B | 2.4 | 2.8 | 2.3 | 2.0 | 1.9 |
| 19 | 4.4 | 2.3 | 1.7 | 2.8 | 2.5 |
| 20 | 4.6 | >4.7 | 4.4 | 3.0 | 3.1 |

EXAMPLES 21 AND 22

Data obtained from a four hour dose response study of S1218 in borate-buffered solution (BBS) with an osmolality of 220 Osm/kg is provided in Table D. Comparative Examples C and D contain 1.3 ppm PHMB and 0.8 ppm PHMB, respectively in corresponding BBS. Example 21 contains 100 ppm S1218 in BBS. Example 22 contains 100 ppm S1218 and 0.8 ppm PHMB in BBS.

TABLE D

Four hour dose response of S1218 with PHMB in BBS.

| Ex. No. | microbe | | | | |
|---|---|---|---|---|---|
| | S. aureus | P. aeruginosa | S. marcescens | C. albicans | F. solani |
| BBS control | 1.4 | 1.2 | 1.3 | 0.6 | 0.3 |
| Comp. Ex. C | 2.6 | 3.1 | 2.6 | 2.6 | 2.2 |
| Comp. Ex. D | 2.4 | 2.8 | 2.4 | 1.8 | 1.8 |
| 21 | >4.9 | 3.4 | 2.0 | 3.3 | 3.3 |
| 22 | 4.4 | 4.7 | 4.8 | 4.7 | 3.3 |

EXAMPLES 23 AND 24

Data obtained from a four hour dose response study of S1218 in a citrate buffered solution with an osmolality of 270 Osm/kg is provided in Table E. Comparative Example E contains 1.3 ppm PHMB in a citrate buffered solution. Example 23 contains 100 ppm S1218 in the citrate buffer. Example 24 contains 100 ppm S1218 and 1.3 ppm PHMB in the citrate buffer.

TABLE E

Four hour dose response of S1218 with PHMB in citrate buffer.

| Ex. No. | microbe | | | | |
|---|---|---|---|---|---|
| | S. aureus | P. aeruginosa | S. marcescens | C. albicans | F. solani |
| citrate control | 1.6 | 1.2 | 1.3 | 0.6 | 0.3 |
| Comp. Ex. E | 3.0 | 4.5 | 2.4 | 0.6 | 0.3 |
| 23 | 4.6 | 3.6 | 1.3 | 2.5 | 2.4 |
| 24 | 4.9 | >4.7 | >4.8 | 3.1 | 3.4 |

EXAMPLES 25 AND 26

Data obtained from a four hour dose response study of S1218 in a phosphate buffered solution with an osmolality of 300 Osm/kg is provided in Table F. Comparative Example G contains 1.3 ppm PHMB in a phosphate buffered solution. Example 25 contains 100 ppm S1218 in BBS. Example 26 contains 100 ppm S1218 and 1.3 ppm PHMB in BBS.

TABLE E

Four hour dose response of S1218 with PHMB in phosphate buffer.

| Ex. No. | microbe | | | | |
|---|---|---|---|---|---|
| | S. aureus | P. aeruginosa | S. marcescens | C. albicans | F. solani |
| phosphate control | 1.4 | 1.2 | 1.1 | 0.6 | 0.4 |
| Comp. Ex. G | 2.3 | 2.4 | 2.0 | 0.7 | 0.3 |
| 25 | >4.8 | 1.2 | 1.1 | 3.8 | 3.0 |
| 26 | 4.6 | >4.7 | >4.6 | 3.7 | 3.4 |

EXAMPLES 27 TO 32

Biocidal data of Table F was obtained from a four hour dose response study for each composition that includes 125 ppm of S-1218 and the stated amounts of L-1010P (in ppm) in a buffered control solution containing 0.6 wt. % sodium borate, 0.2 wt. % glycolic acid, 0.11 wt. % $Na_2EDTA$, 0.5 wt. % propylene glycol, 1.0 wt. % Tetronic®1107, 0.05 wt. % Zwittergent®3-10 and 0.26 wt. % sodium chloride.

TABLE F

Four hour dose response of L-1010P with S-1218

| Ex. No. | microbe | | | | |
|---|---|---|---|---|---|
| | S. aureus | P. aeruginosa | S. marcescens | C. albicans | F. solani |
| control | 1.4 | 1.2 | 1.5 | 0.7 | 0.5 |
| 27, (0) | 2.9 | >4.7 | 1.7 | 3.4 | >4.4 |
| 28, (100) | >4.8 | >4.7 | >4.6 | 4.7 | >4.4 |

TABLE F-continued

Four hour dose response of L-1010P with S-1218

| | microbe | | | | |
|---|---|---|---|---|---|
| Ex. No. | S. aureus | P. aeruginosa | S. marcescens | C. albicans | F. solani |
| 29, (75) | >4.8 | >4.7 | 4.1 | 4.5 | >4.4 |
| 30, (50) | >4.8 | >4.7 | 4.4 | 3.1 | >4.4 |
| 31, (25) | 3.1 | >4.7 | 2.2 | 3.6 | >4.4 |
| 32, (12.5) | 3.2 | 2.2 | 1.1 | 0.5 | >4.4 |

EXAMPLES 33 TO 37

Biocidal data of Table G was obtained from a four hour dose response study for each composition that includes 100 ppm of L-1010P and the stated amounts of S-1218 (in ppm) in a buffered control solution containing 0.6 wt. % sodium borate, 0.2 wt. % glycolic acid, 0.11 wt. % $Na_2EDTA$, 0.5 wt. % propylene glycol, 1.0 wt. % Tetronic® 1107, 0.05 wt. % Zwitergent® 3-10 and 0.26 wt. % sodium chloride.

TABLE G

Four hour dose response of S-1218P with L-1010P

| | microbe | | | | |
|---|---|---|---|---|---|
| Ex. No. | S. aureus | P. aeruginosa | S. marcescens | C. albicans | F. solani |
| control | 1.4 | 1.2 | 1.5 | 0.7 | 0.5 |
| 33, (0) | >4.8 | >4.7 | 2.6 | 1.2 | 2.2 |
| 34, (100) | >4.8 | 4.7 | 4.3 | 2.1 | 3.9 |
| 35, (75) | >4.8 | >4.7 | >4.6 | 3.2 | >4.4 |
| 36, (50) | 4.8 | >4.7 | 3.5 | 2.5 | >4.4 |
| 37, (25) | >4.8 | >4.7 | 3.6 | 1.6 | 4.1 |

EXAMPLES 38 TO 41

Biocidal data of Table H was obtained from a four hour dose response study for each composition that includes 100 ppm of L-1010P and the stated amounts of S-1218 (in ppm) in a buffered control solution containing 0.6 wt. % sodium borate, 0.2 wt. % glycolic acid, 0.11 wt. % $Na_2EDTA$, 0.5 wt. % propylene glycol, 1.0 wt. % Tetronic® 1107, 0.05 wt. % Zwitergent® 3-10 and 0.26 wt. % sodium chloride.

TABLE H

Four hour biocidal data with S-1218P and L-1010P

| Ex. No | S1218 (ppm) | L1010P (ppm) | S. aureus | P. aeruginosa | S. marcescens | C. albicans | F. solani |
|---|---|---|---|---|---|---|---|
| control | — | — | 1.4 | 1.2 | 1.5 | 0.7 | 0.5 |
| 38 | 100 | 80 | >4.8 | >4.7 | >4.6 | 3.6 | >4.4 |
| 39 | 75 | 60 | >4.8 | >4.7 | >4.6 | 2.6 | 3.2 |
| 40 | 50 | 40 | >4.8 | >4.7 | 2.7 | 1.7 | 3.1 |
| 41 | 25 | 20 | 4.1 | 3.6 | 1.8 | 0.9 | 1.6 |

A close review of the biocidal data of Tables F, G and H indicates that a composition comprising both S-1218 and L-1010P possesses excellent biocidal activity across the five microorganisms tested. S-1218 is demonstrated excellent biocidal activity against the fungi F. solani and C. albicans, whereas L-1010P is demonstrated to have excellent biocidal activity against both S. aureus and S. marcescens. Accordingly, a composition containing as little as 75 ppm of S-1218 and 50 ppm of L-1010P is shown to have very strong biocidal activity against all five microorganisms.

EXAMPLES 42 TO 44

Biocidal data of Table J was obtained from a four hour dose response study (with 10% organic soil) for each of the stated compositions. Example compositions 42-44 includes 100 ppm of S-1218 and the stated amounts (in ppm) of polyquatemium-1 in a BBS (control) solution. Comparative Example A is a BBS solution with 100 ppm S-1218 (no PQ-1). Comparative Examples B to D are BBS solutions with the stated amounts of polyquaternium-1 (PQ-1) (no S12-18).

TABLE J

Four hour biocidal data with S-1218P and polyquaternium-1

| Ex. No | PQ-1 (ppm) | S. aureus | P. aeruginosa | S. marcescens | C. albicans | F. solani |
|---|---|---|---|---|---|---|
| control | — | 1.4 | 1.1 | 1.2 | 0.7 | 0.6 |
| comp. A | — | >4.9 | 2.9 | 1.8 | 2.6 | 2.6 |
| comp. B | 2.5 | 3.9 | 3.3 | 3.6 | 2.1 | 2.6 |
| comp. C | 5 | 4.6 | 4.6 | 4.0 | 2.6 | 3.3 |
| comp. D | 10 | 4.1 | >4.6 | 3.9 | 3.2 | 3.6 |
| 42 | 2.5 | 4.7 | >4.6 | >4.7 | 3.3 | 3.2 |
| 43 | 5 | >4.9 | >4.6 | >4.7 | 4.5 | 4.1 |
| 44 | 10 | >4.9 | >4.6 | >4.7 | 4.1 | >4.1 |

Cytotoxicity Study—Sodium Fluorescein Permeability Assay

Figure 2:
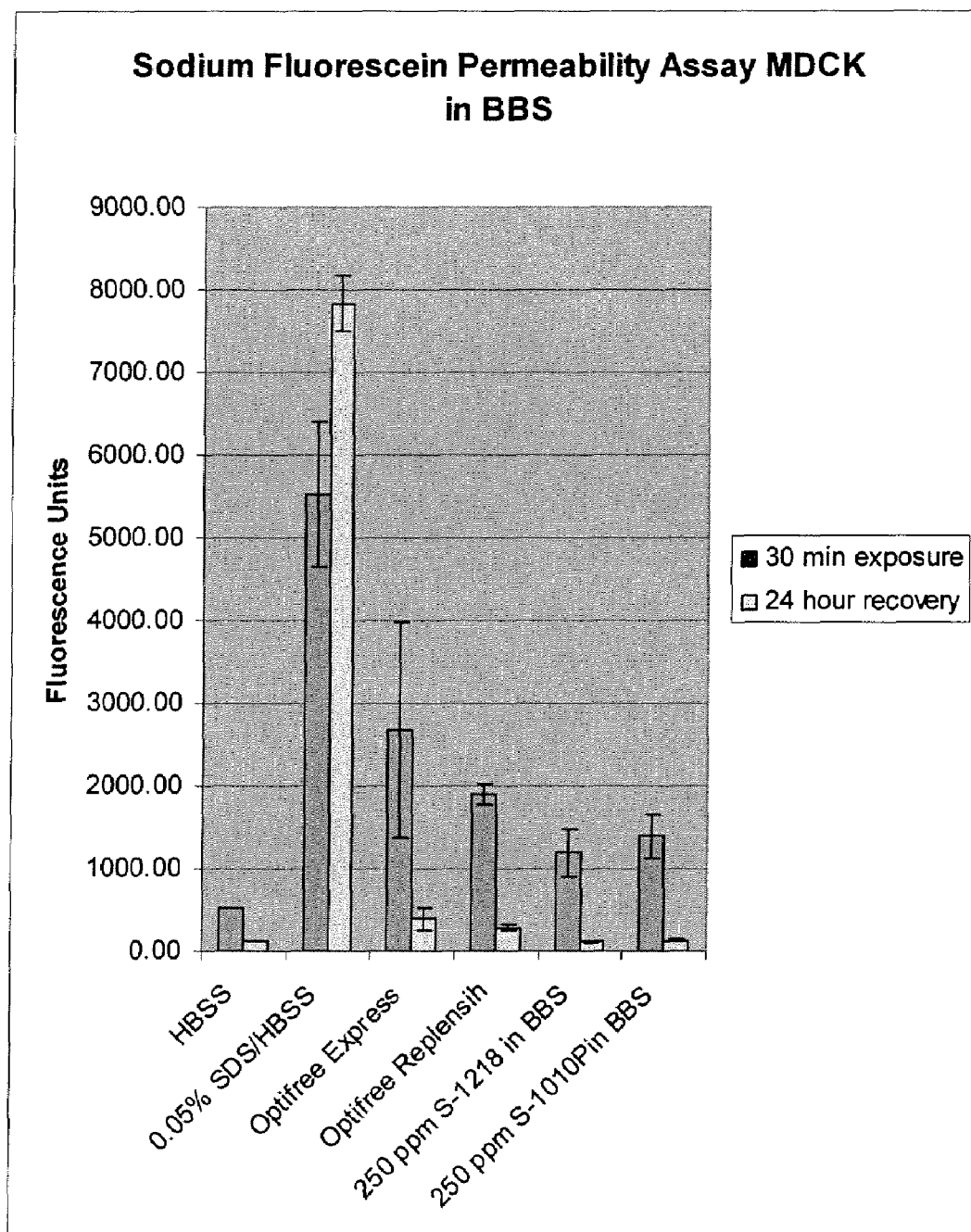
FIG. 2 is a bar graph showing the intensity of fluorescence units of a sodium fluorescein permeability assay with MDCK for two commercial lens care solutions, and compositions of the invention in buffered borate solution.
Figure 3:
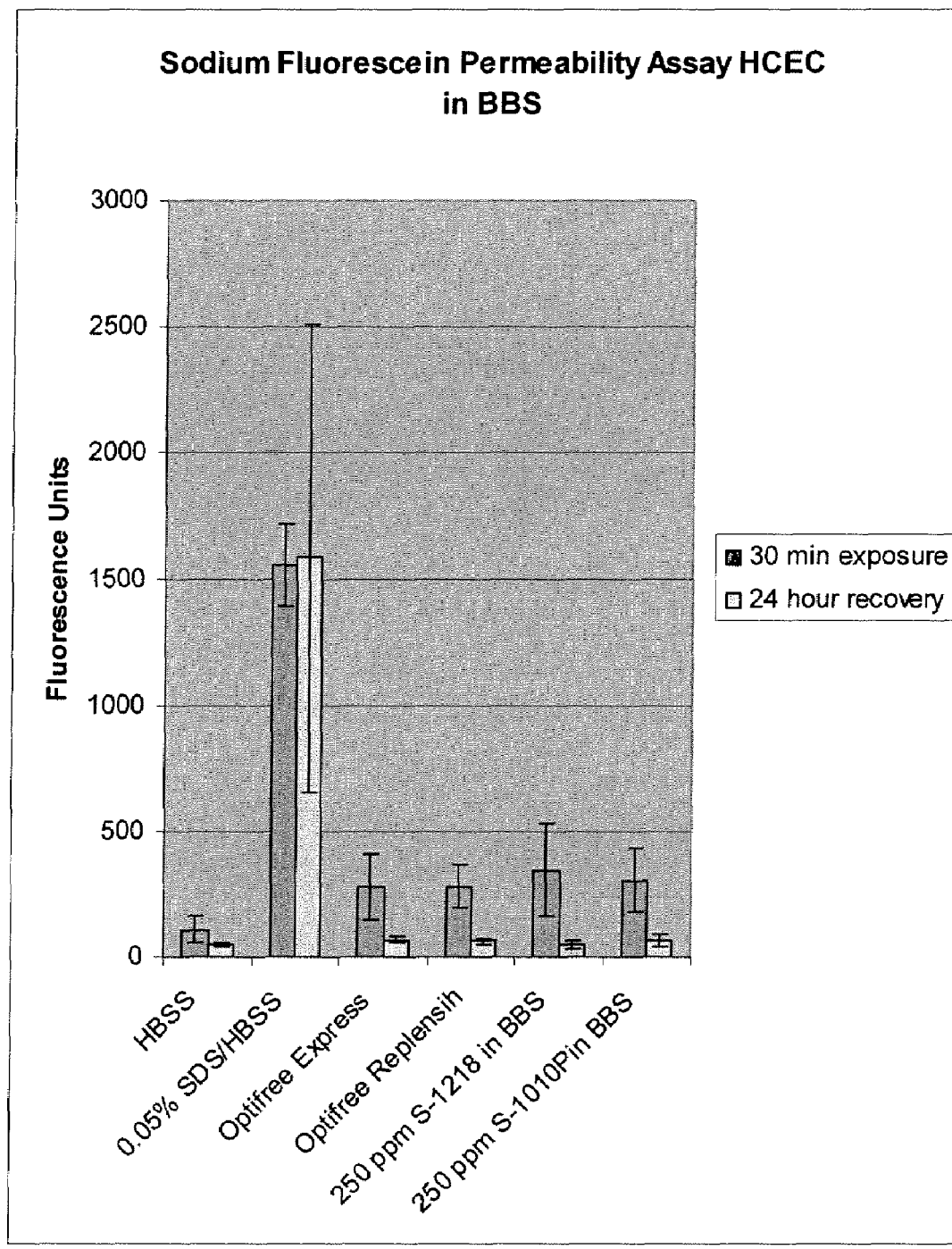
FIG. 3 is a bar graph showing the intensity of fluorescence units of a sodium fluorescein permeability assay with HCEC for two commercial lens care solutions, and compositions of the invention in buffered borate solution.

As demonstrated by the data presented in FIGS. 1 to 3, the compositions of the invention exhibited similar, and even less, staining than two commercial lens care solutions, OptiFree®Express and OptiFree®Replenish, marketed by Alcon Laboratories, Inc.

A cell suspension of 0.5 ml containing $2 \times 10^5$ cells are seeded in Millicell™ HA 12 mm inserts (Millipore, Bedford, Mass.). The inserts are transferred into 24-well plates containing 0.5 ml of medium (MEM or DMEM/F 12) per well. The plates are incubated at 37° C. with five percent $CO_2$ for six days. Fresh media is added to the wells and the inserts on days two through six. On day six, the inserts are used for the permeability assay.

Each prepared insert is gently rinsed three times with approximately 1 to 1.5 ml of Hank's Balanced Salt Solution (HBSS) without phenol red, using a 10 ml syringe without a needle. A small amount of test solution (0.5 mL) is added to separate inserts which are placed in a fresh 24-well plate. Six inserts are used for each test solution. The inserts are incubated in a humidified chamber at 37° C. for 30 minutes. Each series of samples are handled sequentially to allow exact timing of the treatment and subsequent steps. After incubation, each insert is individually rinsed five times with approximately 2 to 2.5 mls HBSS using a 10 ml syringe without a needle.

Sodium fluorescein (0.5 mL, 3 mg/100 ml in HBSS) is added to each insert. The inserts are placed in a 24-well plate with 0.5 ml HBSS in each well and incubated at room temperature for 30 minutes. The inserts are removed from the wells, and the amount of sodium fluorescein is measured using a fluorometer at 485 nm excitation and 535 nm emission. The residual fluorescein is washed off the monolayer three times with HBSS and the cultures are incubated for 24 hours. After the recovery period the cultures are again measured for sodium fluorescein permeability.

We claim:

1. A contact lens care solution comprising:
one or more alkyldimonium hydroxypropyl alkylglucosides of general formula I or general formula II,

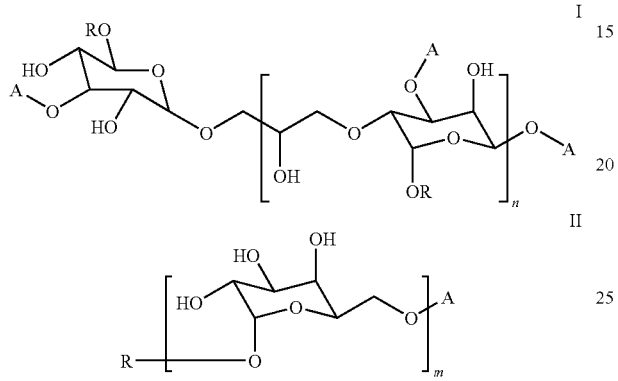

wherein R is a straight or branched $C_8$-$C_{24}$alkyl;
A is —$CH_2CH(OH)CH_2N^+(CH_3)_2R^1X^-$, wherein $R^1$ is a $C_8$-$C_{24}$alkyl and $X^-$ is a common counteranion, n is an average value from 1 to 6 and m is an average value from 1 to 2;
poly(hexamethylene biguanide) at a concentration from 0.05 ppm to 2 ppm; and
a buffer system to maintain the pH of the composition from 7.2 to 8.5, wherein the composition is formulated to clean and disinfect contact lenses.

2. The lens care solution of claim 1 wherein the alkyldimonium hydroxypropyl alkylglucoside of general formula I is selected from the group consisting of
stearyldimoniumhydroxypropyl laurylglucosides chloride,
stearyldimoniumhydroxypropyl laurylglucosides chloride,
stearyldimoniumhydroxypropyl decylglucosides chloride,
lauryldimoniumhydroxypropyl laurylglucosides chloride,
lauryldimoniumhydroxypropyl decylglucosides chloride and
trimoniumhydroxypropyl cocoglucosides chloride.

3. The lens care solution of claim 1 wherein the alkyldimonium hydroxypropyl alkylglucoside of general formula II is selected from the group consisting of
polystearyldimonium hydroxypropyl laurylglucosides chloride,
polystearyldimonium hydroxypropyl decylglucosides chloride,
polylauryldimonium hydroxypropyl laurylglucosides chloride,
polylauryldimonium hydroxypropyl decylglucosides chloride,
polytrimonium hydroxypropyl laurylglucosides chloride and
polytrimonium hydroxypropyl decylglucosides chloride.

4. The lens care solution of claim 1 wherein the alkyldimonium hydroxypropyl alkylglucoside of general formula I or general formula II is present in the solution from 0.001% to 0.05% by weight.

5. A The lens care solution of claim 1 wherein the one or more alkyldimonium hydroxypropyl alkylglucoside includes stearyldimonium hydroxypropyl laurylglucoside.

6. The lens care solution of claim 1 wherein the one or more alkyldimonium hydroxypropyl alkylglucoside includes stearyldimonium hydroxypropyl decylglucoside.

7. The lens care solution of claim 1 further comprising polyquaternium-1 at a concentration from 1 ppm to 10 ppm.

8. The lens care solution of claim 1 further comprising polyquaternium-1 at a concentration from 1 ppm to 3 ppm.

9. The lens care solution of claim 1 further comprising an amphoteric surfactant of general formula A,

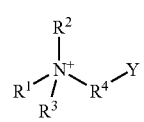

wherein $R^1$ is R or —$(CH_2)_n$—$NHC(O)R$, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally. substituted with hydroxyl; and Y is $CO_2^-$ or $SO_3^-$.

10. A contact lens care solution comprising:
0.001% to 0.1% by weight of one or more alkyldimonium hydroxypropyl alkylglucosides of general formula I or general formula II,

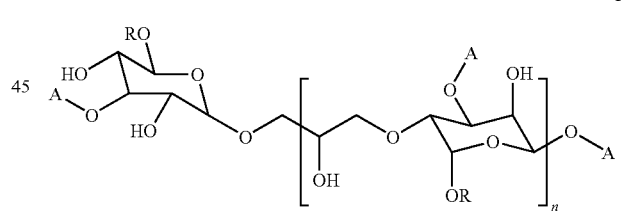

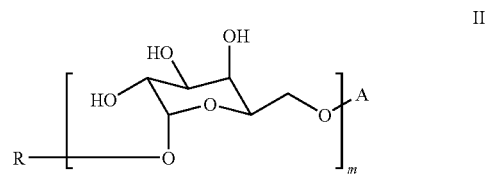

wherein R is a straight or branched $C_8$-$C_{24}$alkyl;
A is —$CH_2CH(OH)CH_2N^+(CH_3)_2R^1X^-$, wherein $R^1$ is a $C_8$-$C_{24}$alkyl and $X^-$ is a common counteranion, n is an average value from 1 to 6 and m is an average value from 1 to 2;
0.3 to 1.3 ppm poly(hexamethylene biguanide);

an amphoteric surfactant of general formula A,

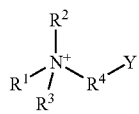

wherein $R^1$ is R or —$(CH_2)_n$—NHC(O)R, wherein R is a $C_8$-$C_{30}$alkyl optionally substituted with hydroxyl and n is 2, 3 or 4; $R^2$ and $R^3$ are each independently selected from the group consisting of hydrogen and $C_1$-$C_4$alkyl; $R^4$ is a $C_2$-$C_8$alkylene optionally substituted with hydroxyl; and Y is $CO_2^-$ or $SO_3^-$; and a buffer system to maintain the pH of the composition from 7.2 to 8.5, wherein the composition is formulated to clean and disinfect contact lenses.

11. The lens care solution of claim 10, wherein the alkyldimonium hydroxypropyl alkylglucoside of general formula II is selected from the group consisting of polystearyldimonium hydroxypropyl laurylglucosides chloride, polystearyldimonium hydroxypropyl decylglucosides chloride, polylauryldimonium hydroxypropyl laurylglucosides chloride, polylauryldimonium hydroxypropyl decylglucosides chloride, polytrimonium hydroxypropyl laurylglucosides chloride and polytrimonium hydroxypropyl decylglucosides chloride.

12. The lens care solution of claim 10 wherein the one or more alkyldimonium hydroxypropyl alkylglucoside includes stearyldimonium hydroxypropyl laurylglucoside or stearyldimonium hydroxypropyl decylglucoside.

13. The lens care solution of claim 10 further comprising a comfort agent selected from the group consisting of propylene glycol, hydroxypropylmethyl cellulose, hydroxylpropyl guar and hyaluronic acid.

14. The lens care solution of claim 13 wherein the comfort agent is hyaluronic acid.

15. The lens care solution of claim 1 wherein the contact lenses are silicone hydrogel contact lenses.

16. A contact lens care solution comprising:

0.001% to 0.1% by weight of one or more alkyldimonium hydroxypropyl alkylglucosides of general formula I or general formula II,

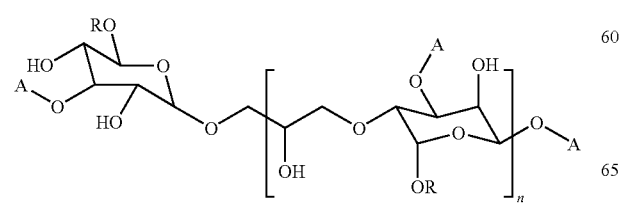

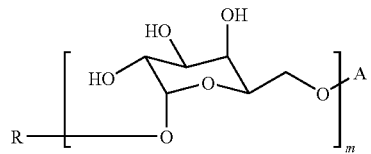

wherein R is a straight or branched $C_8$-$C_{24}$alkyl;

A is —$CH_2CH(OH)CH_2N^+(CH_3)_2R^1X^-$, wherein $R^1$ is a $C_8$-$C_{24}$alkyl and $X^-$ is a common counteranion, n is an average value from 1 to 6 and m is an average value from 1 to 2;

0.5 to 15 ppm of polyquaternium-1; and a buffer system to maintain the pH of the composition from 7.2 to 8.5, wherein the composition is formulated to clean and disinfect contact lenses.

17. The lens care solution of claim 16 wherein the alkyldimonium hydroxypropyl alkylglucoside of general formula II is selected from the group consisting of polystearyldimonium hydroxypropyl laurylglucosides chloride, polystearyldimonium hydroxypropyl decylglucosides chloride, polylauryldimonium hydroxypropyl laurylglucosides chloride, polylauryldimonium hydroxypropyl decylglucosides chloride, polytrimonium hydroxypropyl laurylglucosides chloride and polytrimonium hydroxypropyl decylglucosides chloride.

18. The lens care solution of claim 16 wherein the one or more alkyldimonium hydroxypropyl alkylglucoside includes stearyldimonium hydroxypropyl laurylglucoside or stearyldimonium hydroxypropyl decylglucoside.

19. A contact lens care solution comprising:

one or more alkyldimonium hydroxypropyl alkylglucosides of general formula I or general formula II,

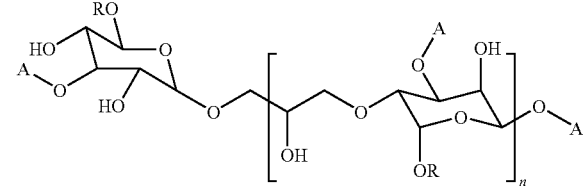

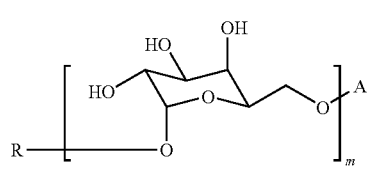

wherein R is a straight or branched $C_8$-$C_{24}$alkyl;

A is —$CH_2CH(OH)CH_2N^+(CH_3)_2R^1X^-$, wherein $R^1$ is a $C_8$-$C_{24}$alkyl and $X^-$ is a common counteranion, n is an average value from 1 to 6 and m is an average value from 1 to 2; and a buffer system to maintain the pH of the composition from 7.2 to 8.5, wherein the composition has an osmolality in the range of at least 200 mOsmol/kg to 400 mOsmol/kg and is formulated to clean and disinfect contact lenses.

20. The lens care solution of claim 19 where in the one or more alkyldimonium hydroxypropyl alkylglucoside includes stearyldimonium hydroxypropyl laurylglucoside or stearyldimonium hydroxypropyl decylglucoside.

21. The lens care solution of claim 19 further comprising a comfort agent selected from the group consisting of propylene glycol, hydroxypropylmethyl cellulose, hydroxylpropyl guar and hyaluronic acid.

22. The lens care solution of claim 19 further comprising a cationic antimicrobial component selected from quaternary ammonium compounds and polymers thereof and low and high molecular weight biguanides.

* * * * *